(12) United States Patent
Li et al.

(10) Patent No.: US 9,176,136 B2
(45) Date of Patent: Nov. 3, 2015

(54) HYBRIDOMA CELL LINE ST03, MONOCLONAL ANTIBODY AGAINST AFLATOXIN BIOSYNTHETIC PRECURSOR STERIGMATOCYSTIN AND USE THEREOF

(71) Applicant: OILCROPS RESEARCH INSTITUTE OF CHINESE ACADEMY OF AGRICULTURE SCIENCES, Wuhan, Hubei (CN)

(72) Inventors: Peiwu Li, Hubei (CN); Min Li, Hubei (CN); Qi Zhang, Hubei (CN); Zhaowei Zhang, Hubei (CN); Xiaoxia Ding, Hubei (CN)

(73) Assignee: OILCROPS RESEARCH INSTITUTE OF CHINESE ACADEMY OF AGRICULTURE SCIENCES, Wuhan, Hubei (CN)

( * ) Notice: Subject to any disclaimer, the term of this patent is extended or adjusted under 35 U.S.C. 154(b) by 0 days.

(21) Appl. No.: 14/666,869

(22) Filed: Mar. 24, 2015

(65) Prior Publication Data

US 2015/0276734 A1    Oct. 1, 2015

(30) Foreign Application Priority Data

Mar. 26, 2014    (CN) .......................... 2014 1 0115952

(51) Int. Cl.
*C07K 16/14*    (2006.01)
*C07K 16/00*    (2006.01)
*C07K 14/38*    (2006.01)
*G01N 33/569*    (2006.01)

(52) U.S. Cl.
CPC .......... *G01N 33/56961* (2013.01); *C07K 16/14* (2013.01); *G01N 2333/38* (2013.01); *G01N 2469/10* (2013.01)

(58) Field of Classification Search
None
See application file for complete search history.

(56) References Cited

FOREIGN PATENT DOCUMENTS

CN    103214572 A    7/2013

*Primary Examiner* — Shafiqul Haq
*Assistant Examiner* — Carmencita M Belei
(74) *Attorney, Agent, or Firm* — Tim Tingkang Xia, Esq.; Locke Lord LLP

(57) ABSTRACT

A hybridoma cell line ST03 having China Center for Type Culture Collection (CCTCC) accession number C2013187, a monoclonal antibody against aflatoxin biosynthetic precursor ST produced by the hybridoma cell line ST03, and the use of the monoclonal antibody. The hybridoma cell line ST03 can be used for preparing a high-titer monoclonal antibody against aflatoxin biosynthetic precursor ST, and the titer of mouse ascites antibody against aflatoxin biosynthetic precursor ST determined by enzyme linked immunosorbent assay (ELISA) can reach $6.4 \times 10^5$. The monoclonal antibody against aflatoxin biosynthetic precursor ST has high sensitivity, has 50% inhibiting concentration $IC_{50}$ to aflatoxin biosynthetic precursor ST of 0.36 ng/mL, has no cross reaction with all of aflatoxin B1, aflatoxin B2, aflatoxin G1, and aflatoxin G2, and can be used for the content determination of aflatoxin biosynthetic precursor ST.

2 Claims, 2 Drawing Sheets

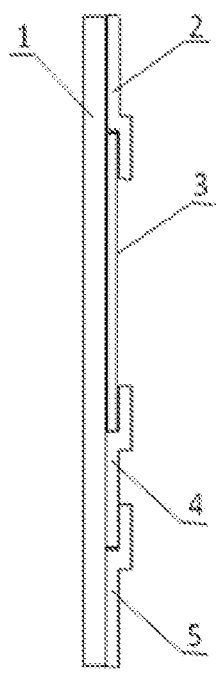
FIG. 3
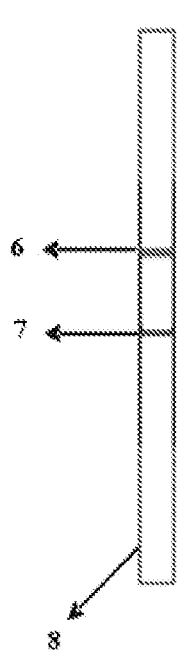 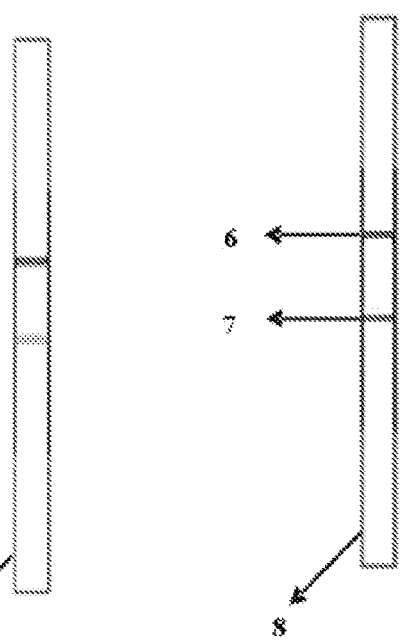
FIG. 4A　　　　FIG. 4B

HYBRIDOMA CELL LINE ST03, MONOCLONAL ANTIBODY AGAINST AFLATOXIN BIOSYNTHETIC PRECURSOR STERIGMATOCYSTIN AND USE THEREOF

CROSS-REFERENCE TO RELATED APPLICATION

This non-provisional application claims priority under 35 U.S.C. §119(a) on Patent Application No. 201410115952.8 filed in P.R. China on Mar. 26, 2014, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to hybridoma cell line ST03, a monoclonal antibody against aflatoxin biosynthetic precursor ST and use thereof.

BACKGROUND OF THE INVENTION

Sterigmatocystin, i.e., ST, as an aflatoxin intermediate, is the early-stage intermediate during the synthesis of aflatoxins. ST is mainly produced by fungi such as *Aspergillus versicolor*, *Aspergillus flavus*, *Aspergillus nidulas*, and *Aspergillus rugulosus*, etc., may contaminate most of grains and forage grasses, and in particular severely contaminate wheat, maize, peanut and forage grasses. The basic structure of aflatoxin biosynthesis precursor ST consists of a difuran ring in connection with xanthone. The precursor has a structure similar to that of aflatoxin, and has toxicity that is second only to that of aflatoxin. Toxicity of ST includes hepatotoxicity, nephrotoxicity, cytogenetic toxicity and strong carcinogenicity. It enters into the human food chain after contaminating foods, and feeds and poses a threat to the health and safety of human. The hazard degree has a positive correlation with the intake of aflatoxin biosynthesis precursor ST. Since China is an area where there is more severe contamination with aflatoxin biosynthesis precursor ST, one of the key points to fortify the food safety is to improve detection of aflatoxin biosynthesis precursor ST in food products and feeds. Accordingly, it is necessary to determine the content of ST in cereals and finished products thereof suspected to be contaminated with the aflatoxin biosynthesis precursor ST.

Currently, methods for detecting aflatoxin biosynthesis precursor ST mainly include thin-layer chromatography (TLC) and liquid chromatography. TLC is easy to operate, and does not require complex and precise instrumentation, but has low sensitivity and low accuracy. Using TLC, a lower limit of detection of aflatoxin biosynthesis precursor ST in rice, maize, and wheat samples is 25 μg/kg and that in soybean and peanut samples is 50 μg/kg. In the recent years, high-performance liquid chromatography (HPLC) has been used widely in the detection of fungal toxins and has also been reported for detecting the aflatoxin biosynthesis precursor ST. However, the application of the HPLC in detection at the basic level has been limited by tedious pre-processing, expensive instrumentation, requirements for stringent operation environment, and professional operators, etc. Therefore, there is a pressing need in the detection field in China to study and develop novel techniques for rapid detection of aflatoxin biosynthesis precursor ST, which is of importance on guaranteeing the safety in food consumption in China.

Immunological analysis techniques, which have been developed in recent years, have been increasingly the focus of rapid detection techniques for pollutants such as aflatoxin, due to advantages such as high sensitivity, short detection time, and easy to operate, etc. However, there are few reports on rapid detection techniques for aflatoxin biosynthesis precursor ST. Antigens and antibodies are the core reagents and the technological sources in immunological analysis techniques. The aflatoxin biosynthesis precursor ST has a molecular weight of 324, belongs to small molecule compounds ($\leq 1000$) and is incapable of directly stimulating an animal to produce antibodies. Only after covalently coupled to a carrier protein such as bovine serum protein (BSA), egg white albumin (OVA), and polylysine, etc., would aflatoxin be converted into an artificial antigen with both reactogenicity and immunogenicity which can stimulate an animal to produce antibodies. Currently, the artificial antigen of aflatoxin biosynthetic precursor ST is obtained mainly via preparation by sodium borohydride reduction, the sensitivity of the antibodies obtained using this artificial antigen is often not high.

SUMMARY OF THE INVENTION

In one aspect, the present invention provides hybridoma cell line ST03, a monoclonal antibody against aflatoxin biosynthetic precursor ST, and use of the monoclonal antibody.

In one embodiment, the present invention relates to the hybridoma cell line ST03. The hybridoma cell line ST03 was deposited with the China Center for Type Culture Collection (CCTCC), Wuhan University, Wuhan, China, on Nov. 13, 2013, and assigned the accession number CCTCC NO. C2013187. It includes a gene sequence encoding the variable region of the heavy chain of the monoclonal antibody against aflatoxin biosynthetic precursor ST as shown in SEQ ID NO:1 in the sequence listing, and a gene sequence encoding the variable region of the light chain of the monoclonal antibody against aflatoxin biosynthetic precursor ST as shown in SEQ ID NO:2 in the sequence listing.

In one embodiment, the present invention relates to a monoclonal antibody against aflatoxin biosynthetic precursor ST secreted by the hybridoma cell line ST03 with the accession number CCTCC NO. C2013187. Variable region of the heavy chain of the monoclonal antibody includes amino acid sequence as shown in SEQ ID NO:3 in the sequence listing. Variable region of the light chain of the monoclonal antibody includes amino acid sequence as shown in SEQ ID No:4 in the sequence listing. The monoclonal antibody can recognize aflatoxin biosynthetic precursor ST, and has 50% inhibiting concentration $IC_{50}$ to aflatoxin biosynthetic precursor ST of 0.36 ng/mL.

In one embodiment, the monoclonal is used in content determination of the aflatoxin biosynthetic precursor ST.

In one embodiment, the hybridoma cell line ST03 is obtained using a two-step screening method. The specific procedures includes: immunizing Balb/c mice with an artificial antigen of aflatoxin biosynthetic precursor ST (aflatoxin biosynthetic precursor ST-BSA) for 4-6 times, followed by boosting the immunization for the last time with the artificial antigen of aflatoxin biosynthetic precursor ST at 2 folds of the former immunizing dose, allowing cell fusion after 3 days, and employing ELISA method to screen the fused cells in two steps: in the first step, screening the positive wells against aflatoxin biosynthetic precursor ST instead of carrier protein BSA using an indirect ELISA method; in the second step, detecting the culture solution of the positive wells which are screened in the first step using an indirect competitive ELISA method with aflatoxin biosynthetic precursor ST as a competitive source, selecting the wells having both relatively high absorbance value and relatively high sensitivity, subcloning using a limiting dilution method, detecting after subcloning by mean of the same two-step screening method, performing such subcloning for 2-3 times, and finally screening to obtain the hybridoma cell line ST03.

In one embodiment, the method of preparing the monoclonal antibody against aflatoxin biosynthetic precursor ST includes the following steps: injecting the obtained hybridoma cell line ST03 into the abdomen of Balb/c mice that was treated with Freund's incomplete adjuvant in advance, collecting the ascites from the mice, and purifying to obtain the monoclonal antibody against aflatoxin biosynthetic precursor ST.

In one embodiment, the above described purification is caprylic acid-ammonium sulfate purification method. The specific operations are: filtering the ascites of the mice with a double-layer filter paper, centrifuging at 4° C. under 12000 r/min for more than 15 minutes (min), obtaining the supernatant, mixing the obtained supernatant of the ascites with 4 folds of volumes of an acetate buffer, slowly adding n-caprylic acid under stirring, in which the volume of n-caprylic acid needed for each milliliter (mL) of ascites is 33 microliter (μL), mixing at room temperature for 30-60 min, allowing the solution to stand at 4° C. for more than 2 hours (h), then centrifuging at 4° C. under 12000 r/min for more than 30 min, discarding the precipitate, filtering the resulting supernatant with double-layer filter paper, adding 0.1 mol/L, pH7.4 phosphate buffer that has 1/10 volume of the filtrate, adjusting the pH of the mixed solution with 2 mol/L sodium hydroxide solution to 7.4, prechilling at 4° C., slowly adding ammonium sulfate to reach a final concentration of ammonium sulfate of 0.277 g/mL, allowing the solution to stand at 4° C. for more than 2 h, then centrifuging at 4° C. under 12000 r/min for more than 30 min, discarding the supernatant, resuspending the precipitates in 0.01 mol/L phosphate buffer of 1/10 volume of the original ascites, filling the solution to a dialysis bag, dialyzing against purified water, freezing the well-dialyzed protein solution in −70° C. freezer, lyophilizing (freeze-drying) with a lyophilizer, collecting the lyophilized powder to obtain the well-purified monoclonal antibody against aflatoxin biosynthetic precursor ST, and storing the antibody into −20° C. freezer.

The acetate buffer is prepared using 0.29 gram (g) sodium acetate and 0.141 mL acetic acid by adding water to a volume of 100 mL. The 0.1 mol/L phosphate buffer is prepared using 0.8 g sodium chloride, 0.29 g disodium hydrogen phosphate dodecahydrate, 0.02 g potassium chloride, and potassium dihydrogen phosphate 0.02 g by adding water to a volume of 100 mL.

Certain embodiments of the present invention, among other things, have the following beneficial advantages.

(1) The hybridoma cell line ST03 provided by the present invention can be used for preparing a high-titer monoclonal antibody against aflatoxin biosynthetic precursor ST, and the titer of mouse ascites antibody against aflatoxin biosynthetic precursor ST determined by enzyme linked immunosorbent assay (ELISA) can reach $6.4 \times 10^5$.

(2) The monoclonal antibody against aflatoxin biosynthetic precursor ST has high sensitivity, has 50% inhibiting concentration $IC_{50}$ to aflatoxin biosynthetic precursor ST of 0.36 ng/mL, and has no cross reaction with all of aflatoxin B1, aflatoxin B2, aflatoxin G1, and aflatoxin G2.

(3) The monoclonal antibody against aflatoxin biosynthetic precursor ST provided by the present invention can be used in the content determination of aflatoxin biosynthetic precursor ST.

These and other aspects of the present invention will become apparent from the following description of the preferred embodiment taken in conjunction with the following drawings, although variations and modifications therein may be effected without departing from the spirit and scope of the novel concepts of the disclosure.

BRIEF DESCRIPTION OF THE DRAWINGS

The accompanying drawings illustrate one or more embodiments of the invention and together with the written description, serve to explain the principles of the invention. Wherever possible, the same reference numbers are used throughout the drawings to refer to the same or like elements of an embodiment, and wherein:

FIG. 3 is a left view of immunochromatographic test paper for the rapid detection of the aflatoxin biosynthetic precursor ST according to one embodiment of the present invention, in which: 1 cardboard; 2 absorbent pad; 3 test pad; 4 gold standard pad; and 5 sample pad.

FIG. 4A and FIG. 4B are the result determination picture for detecting samples using the test paper strip prepared using the monoclonal antibody against aflatoxin biosynthetic precursor ST provided according to one embodiment of the present invention in Example 5, in which: 6 quality control line; 7 test line; 8 control test paper strip; and 9 detection test paper strip.

DETAINED DESCRIPTION OF THE INVENTION

Figure 1:
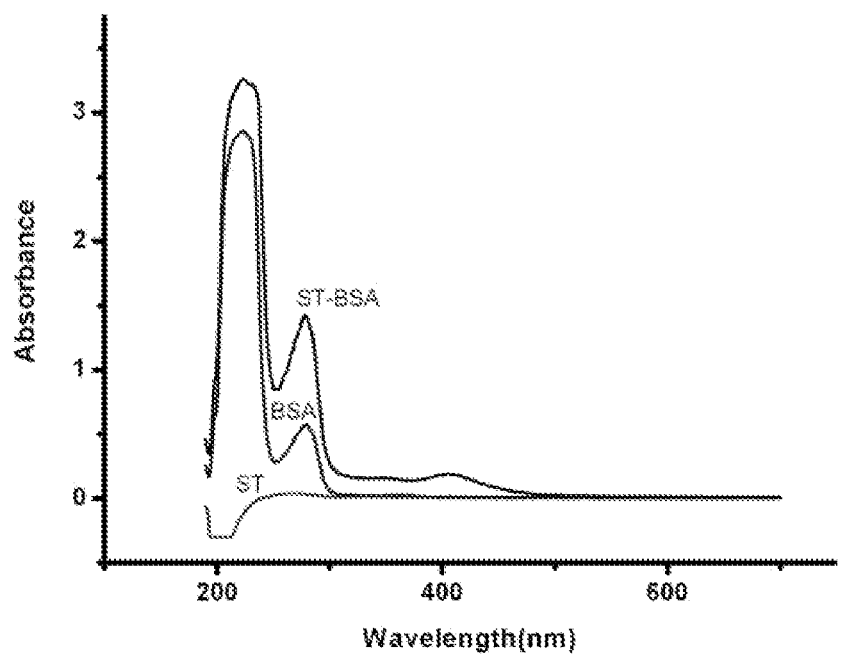
FIG. 1 is an ultraviolet-visible spectrum continuous scanning profile in Example 1, in which ST is the UV-visible spectrum continuous scanning profile of aflatoxin biosynthesis precursor ST; BSA is the ultraviolet-visible spectrum continuous scanning profile of bovine serum albumin; and ST-BSA is the ultraviolet-visible spectrum continuous scanning profile of the artificial antigen of aflatoxin biosynthesis precursor ST.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprising", "including", "carrying", "having", "containing", "involving", and the like are to be understood to be open-ended, i.e., to mean including but not limited to.

The description will be made as to the embodiments of the present invention in conjunction with the accompanying drawings in FIGS. 1-4.

Example 1

Synthesis of Artificial Antigen of Aflatoxin Biosynthetic Precursor ST (1) 0.1 g of commercially-available hydroxyacetic acid (with water content of approximately 1%) was weighed and dissolved in 0.4 mL of trifluoroacetic acid; 1 mg of aflatoxin biosynthesis precursor ST was weighed and dissolved in 0.4 mL of acetonitrile; the solution of the aflatoxin biosynthesis precursor ST in acetonitrile was drawn with a syringe, and pipetted gently into the mixture of the hydroxyacetic acid/trifluoroacetic acid and reacted at room temperature (20° C.-30° C.) for 4 mL with magnetic stirring; the solvent was evaporated rotationally, yielding a light yellowish green oily substance which was the aflatoxin biosynthesis precursor ST hapten.

(2) 1 mg of the aflatoxin biosynthesis precursor ST hapten and 4 mg of N-hydroxylsuccinimide were weighed and placed into a reaction flask, and reacted at room temperature for 1 h with magnetic stirring; 7 mg of carbodiimide was weighed and dissolved in 0.2 mL of 1,4-dioxohextane; the solution of the carbodiimide in 1,4-dioxohextane was added slowly dropwise into the reaction flask and reacted at room temperature for 4 h with magnetic stirring until a white precipitate was generated in the reaction flask; after completion of the reaction, the reactants were kept at room temperature overnight, in the next day, the reactants were subjected to centrifugation at 8000 r/min for 5 min, and the supernatant was obtained; 4 mg of bovine serum albumin (BSA) was weighed and dissolved in 5 mL of phosphate buffered saline (PBS) buffer (0.2 mol/L, pH8.0); the above obtained supernatant was added dropwise into the solution of BSA in PBS, after finishing addition of the supernatant, the reaction was run for 4 h, yielding an complete antigen of aflatoxin biosynthesis precursor ST in aqueous phase.

(3) The complete antigen of aflatoxin biosynthetic precursor ST in aqueous phase from the above-mentioned step (2) was sealed in a dialysis bag and dialyzed for a total of 3 days against 0.01 mol/L, pH8.0 phosphate buffer, where the dialysis solution was replaced once every 12 h; after completion of the last dialysis, the solution in the dialysis bag was divided to fractions, placed in centrifuge tubes, and lyophilized to yield the artificial antigen of aflatoxin biosynthetic precursor ST: aflatoxin biosynthetic precursor ST-bovine serum albumin.

Identification of the Above-Mentioned Synthetic Artificial Antigen of Aflatoxin Biosynthetic Precursor ST:

1. The artificial antigen of aflatoxin biosynthetic precursor ST was identified by the ultraviolet-visible spectrum continuous scanning profile. The results can be seen in FIG. 1. As shown in FIG. 1, the artificial antigen of aflatoxin biosynthetic precursor ST was coupled successfully to the carrier protein, bovine serum albumin. From the absorbance value and the extinction coefficient at the characteristic ultraviolet absorption wavelength of 413 nm for the conjugate, the coupling ratio between the aflatoxin biosynthetic precursor ST and the bovine serum albumin is calculated to be 3.4:1.

2. Immunization in animal had confirmed that anti-aflatoxin biosynthetic precursor ST antibodies were produced.

(1) Immunological experiment in mice: the above-mentioned synthesized aflatoxin biosynthetic precursor ST-bovine serum albumin was formulated with 0.85% of physiological saline into a solution of 0.67 mg/mL. The first immunization was performed by mixing 0.45 mL Freund's complete adjuvant with an equal volume of the formulated aflatoxin biosynthetic precursor ST-bovine serum albumin mentioned above and fully emulsifying the mixture, followed by subcutaneous injecting of 0.3 mL of the preparation (equivalent to 100 μg protein) into each of the 6-8 weeks-old Balb/c mice. Immunization was boosted 1 time every 3 weeks and in the booster immunization, the adjuvant would be changed to Freund's incomplete adjuvant with the remaining of the procedure being the same as those in the first immunization method. Blood was drawn from the tail of the mouse 7-10 days after each booster immunization and the antisera were prepared.

(2) Determination of the antibody titer by non-competitive ELISA assay: the coated antigen, aflatoxin biosynthetic precursor ST-bovine serum albumin, was diluted with a pH9.6 carbonate salt buffer to 0.5 μg/mL. 100 μl of the diluted solution was added into each of the wells of the ELISA plate. The plate was incubated at 4° C. overnight, and then the coating solution was poured off. Each well was washed three times with a typical phosphate-Tween washing liquid and dripped to dry. 200 μl of 1.5% skimmed milk solution was added into each well, and the plate was blocked at 37° C. for 2 h. The blocking solution was poured off, and each well was washed three times and dripped to dry. The antiserum was subjected to double dilution starting from 500 folds, and each well was added with 100 μl. The control wells were set up in parallel with negative serum as the negative control, and 0.15 mol/L pH7.4 phosphate buffer as the blank control. The plate was incubated and moisturized at 37° C. for 2 h, washed three times, and dripped to dry. 100 μl of the enzymatically labelled goat-anti-mouse secondary antibody IgG:HRP diluted at 1:5000 with 0.15 mol/L, pH7.4 phosphate buffer was added into each well, and incubated and moisturized at 37° C. for 2 h. Each well was washed six times and dripped to dry. 100 μl of the reactive substrate solution was added into each well and reacted at 37° C. in the dark for 10-15 min. Then, 50 μl of the 2 mol/L sulphuric acid solution was added into each well to stop the reaction. After 5 min, zero is set using the blank control well, and the absorbance value was measured at 450 nm. The antiserum titer was the dilution factor of the antiserum corresponding to the measured absorbance value of the antiserum two times that of the negative serum. The results were listed in Table 1.

TABLE 1

The antiserum titer against aflatoxin biosynthetic precursor ST

| Dilution fold | 1250 | 2500 | 5000 | 10000 | 20000 | 40000 | 80000 | 160000 | Negative control |
|---|---|---|---|---|---|---|---|---|---|
| Absorbance | 1.16 | 1.14 | 1.07 | 0.85 | 0.62 | 0.43 | 0.39 | 0.14 | 0.09 |

From the data in Table 1, it can be proved that the artificial antigen of aflatoxin biosynthetic precursor ST prepared according to the method of the invention can produce an antiserum with a titer of greater than 80000 after immunization.

(3) ELISA competitive inhibition assay: the operation steps in the ELISA assay were the same as above, except that the antisera subjected to double dilution were replaced with the antiserum solutions containing different concentrations of the standard of the aflatoxin biosynthetic precursor ST. It would confirm that the antibodies in the antisera were capable of binding to the aflatoxin biosynthetic precursor ST if the absorbance value was decreased with increase in the concentrations of the standard of the aflatoxin biosynthetic precursor ST. Results obtained from the competitive ELISA assay were shown in the following Table 2.

TABLE 2

ELISA competitive inhibition assay results against aflatoxin biosynthetic precursor ST

| Inhibition concentrations for aflatoxin biosynthetic precursor ST (ng/mL) | 0 | 0.01 | 0.04 | 0.14 | 0.41 | 1.23 | 3.70 | 11.1 | 33.3 | 100 |
|---|---|---|---|---|---|---|---|---|---|---|
| Absorbance | 0.90 | 0.82 | 0.75 | 0.66 | 0.49 | 0.34 | 0.11 | 0.03 | 0.01 | 0 |

Results of competitive ELISA inhibition assay in Table 2 indicates that the antibody against aflatoxin biosynthetic precursor ST has been produced in the mice, thereby demonstrating that the artificial antigen of aflatoxin biosynthetic precursor ST prepared according to the method in the present invention is successful. Further, it can be seen from Table 2 that $IC_{50}$ value of the antibody against the aflatoxin biosynthetic precursor ST is 0.41 ng/mL. It demonstrates that antibodies with high-sensitivity can be produced after immunization of the mice with the artificial antigen of aflatoxin biosynthetic precursor ST synthesized according to the method in the present invention.

(4) Antibody specificity assay: the operating steps of ELISA were the same as above, except that the antisera subjected to double dilution were replaced with the antiserum solutions containing different concentrations of the standards of aflatoxins B1, B2, G1, and G2. It would confirm that the antibodies in the antisera does not bind to aflatoxins B1, B2, G1, and G2 if there were no regular changes in the absorbance values with the increase in the concentrations of the standards of aflatoxins B1, B2, G1, and G2. Results obtained from the competitive ELISA assay were shown in the following Table 3.

TABLE 3

ELISA competitive inhibition assay against aflatoxins B1, B2, G1, and G2

| | | | | | | | | | | |
|---|---|---|---|---|---|---|---|---|---|---|
| Inhibition concentrations for aflatoxin B1 (ng/mL) | 0 | 0.01 | 0.04 | 0.14 | 0.41 | 1.23 | 3.70 | 11.1 | 33.3 | 100 |
| Absorbance | 0.99 | 1.01 | 0.95 | 0.93 | 1.05 | 0.97 | 0.92 | 0.96 | 0.99 | 0.94 |
| Inhibition concentrations for aflatoxin B2 (ng/mL) | 0 | 0.01 | 0.04 | 0.14 | 0.41 | 1.23 | 3.70 | 11.1 | 33.3 | 100 |
| Absorbance | 1.04 | 1.06 | 0.99 | 1.07 | 1.01 | 1.02 | 1.04 | 1.01 | 1.02 | 1.08 |
| Inhibition concentrations for aflatoxin G1 (ng/mL) | 0 | 0.01 | 0.04 | 0.14 | 0.41 | 1.23 | 3.70 | 11.1 | 33.3 | 100 |
| Absorbance | 1.02 | 1.07 | 1.05 | 1.01 | 0.98 | 1.04 | 1.09 | 1.11 | 1.05 | 1.07 |
| Inhibition concentrations for aflatoxin G2 (ng/mL) | 0 | 0.01 | 0.04 | 0.14 | 0.41 | 1.23 | 3.70 | 11.1 | 33.3 | 100 |
| Absorbance | 1.08 | 1.04 | 1.05 | 1.04 | 1.01 | 1.09 | 1.02 | 1.10 | 1.01 | 1.03 |

Results of the experiment on the specificity of the antibody in Table 3 indicates that the antibody produced in the mice does not bind to aflatoxins B1, B2, G1, and G2, which demonstrated that antibody with high specificity can be produced after immunization of the mice with the artificial antigen of aflatoxin biosynthetic precursor ST synthesized according to the method in the present invention.

Example 2

Preparation of Hybridoma Cell Line ST03

1. Immunization of Animals 8 6-weeks-old Balb/c mice were purchased and immunized with the artificial antigen of aflatoxin biosynthetic precursor ST synthesized in Example 1: aflatoxin biosynthetic precursor ST-BSA. For the first immunization, aflatoxin biosynthetic precursor ST-BSA was emulsified with an equal volume of Freund's complete adjuvant, and subcutaneously injected to the scruff of mice at multiple points. The second immunization was conducted after 3 weeks. Freund's incomplete adjuvant was employed to emulsify an equal volume of aflatoxin biosynthetic precursor ST-BSA, and mice were intraperitoneally injected using the emulsified mixture. The third immunization was performed in an interval of 3 weeks from the second immunization in the same mode. The fourth immunization was performed in an interval of 3 weeks from the third immunization in the same mode, also being intraperitoneal injection. The immunizing dose for 4 times of immunization was the same and was 50 µg per mouse. Blood was taken from the tail vein 8 days after each of the first 3 immunization. Sera were separated, and the antibody titers of the sera of the mice were monitored using the indirect ELISA method. Blood was taken from the tail vein 8 days after the 4th immunization. Sera were separated. The antibody titers of the sera of the mice were detected using the indirect ELISA method, the antibody sensitivity of the sera of the mice was determined using the indirect competitive ELISA method, and the mice corresponding to the sera having relatively high titers and sensitivity were selected to have the last boosting immunization in an immunizing dose of 2 folds of the previous dose.

2. Cell Fusion

Cell fusion was performed 3 days after the last boosting immunization according to a conventional method using 50% (weight percentage) polyethylene glycol, i.e., PEG (with a molecular weight of 1450 dalton) as a fusing agent. The specific procedures is as follows: sacrificing immunized mice under a sterile condition, separating spleen cells, mixing the spleen cells with murine myeloma cells SP2/0 at a ratio of 5-8:1, mixing the cells with RPMI-1640 basic culture solution, fusing with 50% PEG for 1 minute, then slowly adding RPMI-1640 basic culture solution, centrifuging, removing the supernatant, resuspending the fused cells formed from murine spleen cells and murine myeloma cells SP2/0 with 20 mL cell complete medium containing 1% HAT, adding the suspended cells to 80 mL semi-solid medium, mixing uniformly, adding to a 6-well culture plate with 1.5 mL in each well, and culturing in 37° C. carbon dioxide incubator. The cell complete medium containing 1% HAT includes 20% (volume percentage) fetal bovine serum, 75% (volume percentage) RPMI-1640 basic culture medium, 1% (weight percentage) L-glutamine, 1% (volume percentage) HEPES, 1% (volume percentage) double antibiotics (10000 units penicillin per milliliter and 10000 µg streptomycin per milliliter), 2% (weight percentage) growth factor, and 1% (weight percentage) hypoxanthine-aminopterin-thymidine (i.e., HAT). The semi-solid medium is a cell complete culture medium containing 1% (mass percentage) methyl cellulose. The RPMI-1640 basic culture medium, HEPES, the double antibiotics, and L-glutamine were purchased from Hyclone Inc. The 1% hypoxanthine-aminopterin-thymidine (i.e., HAT) and methyl cellulose were purchased from Sigma-Aldrich Inc.

3. Screening and Cloning of Cell Lines 2-3 weeks after cell fusion, when the cell colonies were grown until they were visible to the human naked eye, the clones were pipetted out from the culture medium using a micropipette and transferred to a 96-well cell culture plate for liquid scale up culture. Each well is transferred with 1 clone. When the cells spread ½-⅔ of the bottom of the well, the culture supernatant was pipetted out for positive detection, i.e., antibody detection. The culture wells having grown hybridoma cells were screened using ELISA method. The screening was carried out in two steps: in the first step, screening the positive wells against aflatoxin biosynthetic precursor ST, but not against carrier protein BSA. using the indirect ELISA method; in the second step, detecting the positive wells which were screened in the first step using the indirect competitive ELISA method, where aflatoxin biosynthetic precursor ST was used as a competitive source, the wells having both relatively high absorbance value and relatively high sensitivity (the relatively high absorbance value refers to the final measured values of the positive control wells, i.e., the wells having a competitive source of 0, are relatively high, and the relatively high sensitivity refers to the concentration of the competitive source when the inhibition ratio is 50%, that is, the $IC_{50}$ value is relatively small) were selected, and subcloning using a limiting dilution method was performed. Detecting after subcloning was performed by the same two-step method. Such subcloning were carried out for 2-3 times to obtain the hybridoma cell line ST03.

Example 3

Sequencing of the Variable Region of the Monoclonal Antibody Produced from the Hybridoma Cell Line ST03 Against Aflatoxin Biosynthetic Precursor ST (1) Extraction of the total RNA: the total RNA extraction kit from Qiagen Inc. was used according to the instructions to obtain the total RNA of hybridoma cell line ST03.

(2) Synthesis of cDNA: using the total RNA obtained in step (1) as the template and oligo $(dT)_{15}$ as the primer, and performing reverse transcription according to the instructions of reverse transcriptase SuperScript™-2 II to synthesize the first strand of cDNA, in which the primer oligo $(dT)_{15}$ was purchased from Invitrogen Inc.

(3) Cloning of the variable region genes by PCR method: designing the primers according to the conserved sites of the gene sequences of mouse antibodies in GENEBANK, and amplifying the variable region genes of the light chains and the heavy chains using cDNA as the template. PCR protocols were: 94° C. 30 second (s), 58° C. 1 min, 72° C. 1 min, amplifying for 30 cycles, and finally extending at 72° C. for 10 min. PCR products were separated using 1% (weight percentage) agarose gel electrophoresis. The recovered DNA fragments were then purified using a kit, ligated to vector pMD18-T, and used to transform the competent cells of *Escherichia coli* DH5α. The positive clones are selected, and sent to Shanghai Sunny Biotechnology Co., Ltd. for sequencing. The sequences of primers were respectively as follows. The primers for the heavy chain variable region are: 5'-AGG TSM ARC TGC AGS AGT CWG G-3' (22 mer, SEQ ID NO:5) and 5'-TGA GGA GAC GGT GAC CGT GGT CCC TTG GCC CC-3' (32 mer, SEQ ID NO:6), where S, M, R and W were degeneracy bases, M=A/C, R=A/G, S=C/G, W=A/T. The primers for the light chain variable region are: 5'-GAC ATT GAG CTC ACC CAG TCT CCA-3' (24 mer, SEQ ID NO:7) and 5'-CCG TTT TAT TTC AGC TTG GTC CC-3' (24 mer, SEQ ID NO:8).

The results of the obtained gene sequences: the gene sequence encoding the heavy chain variable region is 336 bp in length, and has a sequence as shown in SEQ ID NO:1. The heavy chain variable region deduced from the gene sequence composes 112 amino acids and has a sequence as shown in SEQ ID NO:3. The gene sequence encoding the light chain variable region is 324 bp in length, and has a sequence as shown in SEQ ID NO:2. The light chain variable region deduced from the gene sequence composes 108 amino acids, and has a sequence as shown in SEQ ID NO:4.

Example 4

Preparation, Purification, and Characterization of the Monoclonal Antibody Against Aflatoxin Biosynthetic Precursor ST The monoclonal antibody hybridoma cell line ST03 obtained in Example 2 was injected to Balb/c mice which were treated with Freund's incomplete adjuvant in advance. The ascites were collected from the mice. Antibodies were purified by caprylic acid-ammonium sulfate method. The specific purification steps were: filtering the ascites of the mice with a double-layer filter paper, centrifuging at 4° C. under 12000 r/min for 15 min, pipetting the supernatant, mixing the obtained supernatant of the ascites with 4 folds of volumes of acetate buffer, slowly adding n-caprylic acid under stirring, in which the volume of n-caprylic acid needed for per milliliter of ascites was 33 µL, mixing at room temperature for 30 min, standing at 4° C. for 2 h, then centrifuging at 4° C. under 12000 r/min for 30 min, discarding the precipitate, filtering the resulting supernatant with a double-layer filter paper, adding 0.1 mol/L, pH7.4 phosphate buffer which has 1/10 volume of the filtrate, adjusting the pH of the mixed solution with 2 mol/L sodium hydroxide solution to 7.4, prechilling at 4° C., slowly adding ammonium sulfate to reach a final concentration of ammonium sulfate of 0.277 g/mL, standing at 4° C. for 2 h, then centrifuging at 4° C. under 12000 r/min for 30 min, discarding the supernatant, resuspending the precipitates in 0.01 mol/L phosphate buffer of 1/10 volume of the original ascites, filling a dialysis bag with the re-suspended solution, dialyzing against purified water, freezing the well-dialyzed protein solution in −74° C. freezer, lyophilizing (freeze-drying) with a lyophilizer, collecting the lyophilized (freeze-dried) powder to obtain the well-purified monoclonal antibody against aflatoxin biosynthetic precursor ST, and storing the antibody into −20° C. freezer for later use.

The acetate buffer was prepared using 0.29 g sodium acetate and 0.141 mL acetic acid, by adding water to reach a volume of 100 mL. The 0.1 mol/L phosphate buffer was prepared using 0.8 g sodium chloride, 0.29 g disodium hydrogen phosphate dodecahydrate, 0.02 g potassium chloride, and potassium dihydrogen phosphate 0.02 g. by adding water to reach a volume of 100 mL.

A commercially available subgroup identification kit was used to identify the subgroup of the monoclonal antibody against aflatoxin biosynthetic precursor ST secreted by hybridoma cell line ST03 as IgG2a.

The antibody titer obtained from the ascites of the Balb/c mice injected with ST03 hybridoma cells measured by a conventional noncompetitive enzyme linked immunosorbent assay (ELISA) method can reach $6.4 \times 10^5$. That is to say, the measured result of the solution of the monoclonal antibody against aflatoxin biosynthetic precursor ST which was diluted in $6.4 \times 10^5$ folds was still positive. The sensitivity of the antibody to aflatoxin biosynthetic precursor ST measured by a conventional indirect competitive ELISA method was 0.36 ng/mL. The antibody has no cross reaction with all of aflatoxin B1, aflatoxin B2, aflatoxin G1, and aflatoxin G2.

Example 5

Use of the Antibody

The monoclonal antibody against aflatoxin biosynthetic precursor ST secreted by hybridoma cell line ST03 was used for preparing immunochromatographic test paper strip for aflatoxin biosynthetic precursor ST. The preparation method includes the following steps.

(1) Preparing an Absorbent Pad

Cutting an absorbent paper into a specification of 15-20 mm length and 3.4 mm width to obtain the absorbent pad.

(2) Preparing a Test Pad

Preparing the test pad: nitrocellulose membrane HF135 of 25 mm length and 3.4 mm width (purchased from EMD Millipore, Mass., U.S.) was used as the test pad.

Coating a Test Line:

The aflatoxin biosynthetic precursor ST-BSA was prepared into a coating solution A having a concentration of 0.4 mg/mL. The coating solution A was transversely coated onto the nitrocellulose membrane along a position at a distance of 15 mm from the top end of the nitrocellulose membrane by spot spraying to give the test line. The coating amount of the artificial antigen of aflatoxin biosynthetic precursor ST, i.e., ST-BSA, needed for each centimeter of the test line was 200 ng. The test line was dried at 37° C. for 30 minutes.

The coating solution A was prepared using 4 mg aflatoxin biosynthetic precursor ST-BSA synthesized by the inventors, 0.1 g bovine serum albumin, 0.002 g sodium azide, 0.08 g sodium chloride, 0.029 g disodium hydrogen phosphate dodecahydrate, 0.002 g potassium chloride, and 0.002 g potassium dihydrogen phosphate, by adding water to reach a volume of 10 mL.

Coating a Quality Control Line:

The rabbit-anti-mouse polyclonal antibody was prepared into a coating solution B having a concentration of 0.25 mg/mL. The coating solution B was transversely coated onto the nitrocellulose membrane along a position at a distance of 6 mm from the test line by spot spraying to give the quality control line. The coating amount of the rabbit-anti-mouse polyclonal antibody needed for each centimeter of the quality control line was 100 ng. The control line was dried at 37° C. condition for 1 hour.

The coating solution B was prepared using 2.5 mg commercially available rabbit-anti-mouse polyclonal antibody (purchased from Sigma-Aldrich, MO, U.S.), 0.002 g sodium azide, 0.08 g sodium chloride, 0.029 g disodium hydrogen phosphate dodecahydrate, 0.002 g potassium chloride, and 0.002 g potassium dihydrogen phosphate, by adding water to reach a volume of 10 mL.

(3) Preparing a Sample Pad

Glass fiber membrane was cut into a specification of 13 mm length and 3.4 mm width, moistened in blocking solution A, took out, and dried at 37° C. for 6 hours to obtain a sample pad. The obtained sample pad was placed in a drier and stored at room temperature.

The blocking solution A was prepared using 2 g bovine serum albumin, 2.5 g sucrose, 0.02 g sodium azide, 0.8 g sodium chloride, 0.29 g disodium hydrogen phosphate dodecahydrate, 0.02 g potassium chloride, and 0.02 g potassium dihydrogen phosphate, by adding water to reach a volume of 100 mL.

(4) Preparing a Gold Standard Pad

Glass fiber membrane was cut into a specification of 10 mm length and 3.4 mm width, moistened in blocking solution B, took out, and dried at 37° C. for 6 hours. The solution of nanogold-labeled monoclonal antibody against aflatoxin biosynthetic precursor ST was transversely coated onto the glass fiber membrane by spot spraying, in which the nanogold-labeled monoclonal antibody against aflatoxin biosynthetic precursor ST needed for each centimeter of spraying length was 350 ng. Then the glass fiber membrane is lyophilized under vacuum for 2.5 h, and placed in a drier and stored at room temperature.

The blocking solution B was prepared using 2 g bovine serum albumin, 2.5 g sucrose, 1.6775 g sodium chloride, 50 µL Tween-20, 0.5 g polyvinylpyrrolidone, 0.02 g sodium azide, 0.29 g disodium hydrogen phosphate dodecahydrate, 0.02 g potassium chloride, and 0.02 g potassium dihydrogen phosphate, by adding water to reach a volume of 100 mL.

The particular preparation method for the solution of the nanogold-labeled monoclonal antibody against aflatoxin biosynthetic precursor ST includes: weighing 50.0 mL of 0.01% mass concentration of nanogold solution, adjusting pH value using 425 µL of 0.1 mol/L potassium carbonate aqueous solution; slowly adding 2.5 mL of 0.1 mg/mL aqueous solution of monoclonal antibody against aflatoxin biosynthetic precursor ST under stirring, allowing reaction for 30 min under continuous stirring; adding an aqueous solution of 10% mass concentration of bovine serum albumin, until the final mass concentration of the bovine serum albumin was 1%, continuing to stir for 30 min; standing at 4° C. for 2 h, centrifuging under 1500 r/min for 15 min, taking the supernatant and discarding the precipitate; centrifuging the supernatant under 12000 r/min for 30 min, discarding the supernatant, and adding 30.0 mL labelling washing stock solution; centrifuging under 12000 r/min again for 30 min, discarding the supernatant, resuspending the precipitate using the labelling washing stock solution to obtain 5.0 mL concentrated solution of nanogold labelled monoclonal antibody against aflatoxin biosynthetic precursor ST, and storing in 4° C. refrigerator for future use, where the mass concentration of the nanogold labelled monoclonal antibody against aflatoxin biosynthetic precursor ST was 0.05 mg/mL.

The particle size of nanogold in the nanogold solution was 15 nm. The 0.1 mol/L potassium carbonate aqueous solution was prepared by: dissolving 13.8 g potassium carbonate in purified water to reach a volume of 1000 mL, and filtering with 0.22 µm filter membrane. The 0.1 mg/mL aqueous solution of the monoclonal antibody against aflatoxin biosynthetic precursor ST was prepared by: dissolving 1 mg monoclonal antibody against aflatoxin biosynthetic precursor ST prepared in the present invention in 10 ml, purified water. The 10% bovine serum albumin was prepared by: dissolving 10 g bovine serum albumin in 100 mL purified water and filtering with 0.22 µm filter membrane. The labelling washing stock solution was prepared by: weighing 2.0 g polyethylene glycol-20000, 0.2 g sodium azide, 0.1235 g boric acid, adding purified water to reach a volume of 1000 mL and filtering with 0.22 µm filter membrane.

(5) Assembling a Test Paper Strip

Figure 2:
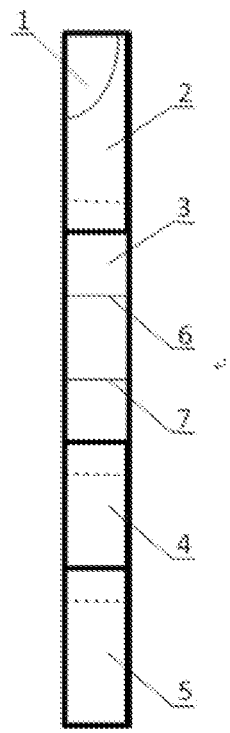
FIG. 2 is a front view of immunochromatographic test paper for the rapid detection of the aflatoxin biosynthetic precursor ST according to one embodiment of the present invention, in which: 1 cardboard; 2 absorbent pad; 3 test pad; 4 gold standard pad; 5 sample pad; 6 quality control line; and 7 test line.

The absorbent pad, test pad, gold standard pad, and sample pad were sequentially adhered to one side of a cardboard from top to bottom. Referring to FIG. 2 and FIG. 3, the adjacent pads were overlapped at their joints with a joint length of 1-2 mm, so as to obtain the immunochromatographic test paper strip of aflatoxin biosynthetic precursor ST.

Use of the Above-Prepared Immunochromatographic Test Paper Strip of Aflatoxin Biosynthetic Precursor ST:

Treatment of a wheat sample: 20 g of wheat sample was taken and ground with a grinder. 80 ml, 70% (volume fraction) methanol-water was added to the ground wheat sample, and the mixture is allowed to react for 2 minutes under stirring to give a mixed solution of the sample. The mixed solution is manually shaken for 3 minutes, and filtered using a double-layer filter paper. 2 mL of filtrate was collected, and 6 mL purified water was added to dilute the filtrate. The filtrate and the purified water was mixed uniformly to obtain a sample solution for detection.

Detection of the wheat sample using an aflatoxin biosynthetic precursor ST test paper strip: wheat sample detection liquids 1# and 2# were prepared respectively. 100 µL 1# and 2# wheat sample solution for detection were pipetted respectively, and each added dropwise to a sample pad of the immunochromatographic test paper strip of aflatoxin biosynthetic precursor ST. Meanwhile, 100 µL blank wheat detection liquid, which is free of aflatoxin biosynthetic precursor ST, was added dropwise to another sample pad of immunochromatographic strip of aflatoxin biosynthetic precursor ST, to form the control test paper strip. The results were read after 15 minutes.

Detection results (shown in FIG. 4A and FIG. 4B): both the quality control line and the test line of the control test paper strip showed red bands. Referring to FIG. 4A, the quality control line of 1# test paper strip showed a red band, but the color of its test line was lighter than that of the test line of the control test paper strip, which indicated that the content of aflatoxin biosynthetic precursor ST in the detection liquid of 1# wheat sample was equal to or higher than 0.37 ng/mL and lower than 1.5 ng/mL. Referring to FIG. 4B, the quality control line of 2# test paper strip showed a red line, but its test line did not show color, which indicated that the content of aflatoxin biosynthetic precursor ST in the detection liquid of 2# wheat sample was higher than 1.5 ng/mL.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A hybridoma cell line ST03, deposited at the China Center for Type Culture Collection (CCTCC) with the CCTCC accession number of C2013187.

2. A monoclonal antibody against aflatoxin biosynthetic precursor ST, obtained from the hybridoma cell line ST03 of claim 1.

* * * * *

```
                              SEQUENCE LISTING

<160> NUMBER OF SEQ ID NOS: 8

<210> SEQ ID NO 1
<211> LENGTH: 336
<212> TYPE: DNA
<213> ORGANISM: Mus musculus

<400> SEQUENCE: 1
gtgcaactgc aggagtctgg ggctgaactg gcaagacctg gggcctcagt gaagatgtcc      60
tgcaaggctt ctggctacac ctttactacc tacacgatac actggctaaa acagaggcct     120
ggacagggtc tggaatggat tggatacatt aatcctagca gtggttatac taattacaat     180
cagaaattca aggacaaggc cacattgact gcagacaaat cctccagcac agcctacatg     240
caactgagca gcctgacatc tgaggactct gcagtctatt actgtactag aaggggggac     300
tactggggcc aagggaccac ggtcaccgtc tcctca                               336

<210> SEQ ID NO 2
<211> LENGTH: 324
<212> TYPE: DNA
<213> ORGANISM: Mus musculus

<400> SEQUENCE: 2
gacattgagc tcacccagtc tccatcctcc ttatctgcct ctctgggaga aagagtcagt      60
ctcacttgtc ggacaagtca ggacattggt agtagtttag cctggcttca gcagaaatca     120
gatggaagta ttaaacgcct gatctccgcc acatccagtt tagaatctgg tgtcccaaa      180 aggttcagcg gcagtaggtc tgggtcagat tattctctca ccatcagcag ccttgagtct     240
gaagattttg ttgactatta ctgtctacaa tatgctaatt ttccgctcac gttcggttct     300
gggaccaagc tggaaataaa acgg                                            324

<210> SEQ ID NO 3
<211> LENGTH: 112
<212> TYPE: PRT
<213> ORGANISM: Mus musculus

<400> SEQUENCE: 3

Val Gln Leu Gln Glu Ser Gly Ala Glu Leu Ala Arg Pro Gly Ala Ser
1               5                   10                  15

Val Lys Met Ser Cys Lys Ala Ser Gly Tyr Thr Phe Thr Thr Tyr Thr
            20                  25                  30

Ile His Trp Leu Lys Gln Arg Pro Gly Gln Gly Leu Glu Trp Ile Gly
```

```
                35                  40                  45
Tyr Ile Asn Pro Ser Ser Gly Tyr Thr Asn Tyr Asn Gln Lys Phe Lys
         50                  55                  60

Asp Lys Ala Thr Leu Thr Ala Asp Lys Ser Ser Ser Thr Ala Tyr Met
 65                  70                  75                  80

Gln Leu Ser Ser Leu Thr Ser Glu Asp Ser Ala Val Tyr Tyr Cys Thr
                 85                  90                  95

Arg Arg Gly Asp Tyr Trp Gly Gln Gly Thr Thr Val Thr Val Ser Ser
            100                 105                 110

<210> SEQ ID NO 4
<211> LENGTH: 108
<212> TYPE: PRT
<213> ORGANISM: Mus musculus

<400> SEQUENCE: 4

Asp Ile Glu Leu Thr Gln Ser Pro Ser Ser Leu Ser Ala Ser Leu Gly
 1               5                  10                  15

Glu Arg Val Ser Leu Thr Cys Arg Thr Ser Gln Asp Ile Gly Ser Ser
             20                  25                  30

Leu Ala Trp Leu Gln Gln Lys Ser Asp Gly Ser Ile Lys Arg Leu Ile
         35                  40                  45

Ser Ala Thr Ser Ser Leu Glu Ser Gly Val Pro Lys Arg Phe Ser Gly
     50                  55                  60

Ser Arg Ser Gly Ser Asp Tyr Ser Leu Thr Ile Ser Ser Leu Glu Ser
 65                  70                  75                  80

Glu Asp Phe Val Asp Tyr Tyr Cys Leu Gln Tyr Ala Asn Phe Pro Leu
                 85                  90                  95

Thr Phe Gly Ser Gly Thr Lys Leu Glu Ile Lys Arg
            100                 105

<210> SEQ ID NO 5
<211> LENGTH: 22
<212> TYPE: DNA
<213> ORGANISM: Artificial Sequence
<220> FEATURE:
<223> OTHER INFORMATION: Heavy chain 5' primer

<400> SEQUENCE: 5
aggtsmarct gcagsagtcw gg                                            22

<210> SEQ ID NO 6
<211> LENGTH: 32
<212> TYPE: DNA
<213> ORGANISM: Artificial Sequence
<220> FEATURE:
<223> OTHER INFORMATION: Heavy chain 3' primer

<400> SEQUENCE: 6
tgaggagacg gtgaccgtgg tcccttggcc cc                                 32

<210> SEQ ID NO 7
<211> LENGTH: 24
<212> TYPE: DNA
<213> ORGANISM: Artificial Sequence
<220> FEATURE:
<223> OTHER INFORMATION: Light chain 5' primer

<400> SEQUENCE: 7
gacattgagc tcacccagtc tcca                                          24
```

```
<210> SEQ ID NO 8
<211> LENGTH: 24
<212> TYPE: DNA
<213> ORGANISM: Artificial Sequence
<220> FEATURE:
<223> OTHER INFORMATION: Light chain 3' primer

<400> SEQUENCE: 8
ccgttttatt tccagcttgg tccc                                          24
```